United States Patent
Yamada et al.

(10) Patent No.: US 9,662,477 B2
(45) Date of Patent: *May 30, 2017

(54) MICROACCESS KIT COMPRISING A TAPERED NEEDLE

(71) Applicant: TERUMO MEDICAL CORPORATION, Somerset, NJ (US)

(72) Inventors: Yasutake Yamada, Bear, DE (US); Linda E. Trask, Newark, DE (US)

(73) Assignee: TERUMO MEDICAL CORPORATION, Somerset, NJ (US)

(*) Notice: Subject to any disclaimer, the term of this patent is extended or adjusted under 35 U.S.C. 154(b) by 156 days.

This patent is subject to a terminal disclaimer.

(21) Appl. No.: 14/582,735

(22) Filed: Dec. 24, 2014

(65) Prior Publication Data

US 2015/0182730 A1 Jul. 2, 2015

Related U.S. Application Data

(63) Continuation of application No. 13/421,404, filed on Mar. 15, 2012, now Pat. No. 9,011,381.

(60) Provisional application No. 61/453,894, filed on Mar. 17, 2011.

(51) Int. Cl.
| A61M 5/178 | (2006.01) |
| A61M 25/06 | (2006.01) |
| A61M 29/00 | (2006.01) |
| A61M 5/32 | (2006.01) |
| A61M 25/00 | (2006.01) |

(52) U.S. Cl.
CPC .......... *A61M 25/06* (2013.01); *A61M 5/3286* (2013.01); *A61M 29/00* (2013.01); *A61M 25/0068* (2013.01)

(58) Field of Classification Search
CPC .. A61M 25/0068; A61M 25/06; A61M 29/00; A61M 5/3286
USPC ..................................................... 604/164.01
See application file for complete search history.

(56) References Cited

U.S. PATENT DOCUMENTS

| 4,909,800 A | 3/1990 | Gross | |
| 5,951,528 A * | 9/1999 | Parkin ................... | A61M 5/329 600/4 |
| 2007/0060927 A1* | 3/2007 | Longson ............. | A61M 25/065 606/108 |
| 2007/0179455 A1* | 8/2007 | Geliebter .............. | A61M 5/329 604/272 |

FOREIGN PATENT DOCUMENTS

| JP | 11-33028 A | 2/1999 |
| JP | 2000-176009 A | 6/2000 |

OTHER PUBLICATIONS

Office Action with respect to the Japanese Patent Application No. JP2012-061091 as counterpart, dated Mar. 8, 2016, 5 pages.

(Continued)

*Primary Examiner* — Jason Flick

(57) ABSTRACT

The present technology is directed to introducer needle assemblies comprising a tapered needle; as well as to kits comprising a tapered needle, a guidewire and a dilator and sheath; as well as to methods of introducing a dilator to the interior of a patient's body as part of an interventional procedure.

13 Claims, 13 Drawing Sheets

(56) References Cited

OTHER PUBLICATIONS

Translation of the Office Action with respect to the Japanese Patent Application No. JP2012-061091 as a counterpart, dated Mar. 8, 2016, 6 pages.
Machine translation of JP2000-176009A, dated Jun. 27, 2000.
Machine translation of JP11-33028A, dated Feb. 9, 1999.

* cited by examiner

FIG. 4
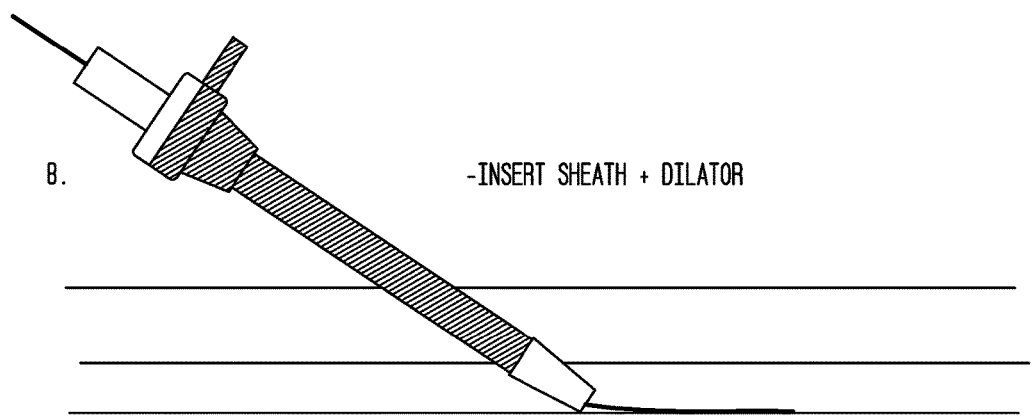
8. —INSERT SHEATH + DILATOR
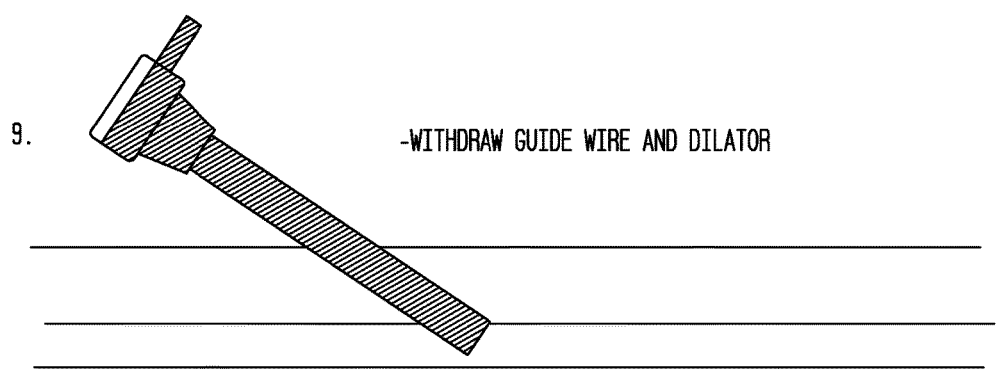
9. —WITHDRAW GUIDE WIRE AND DILATOR

FIG. 6
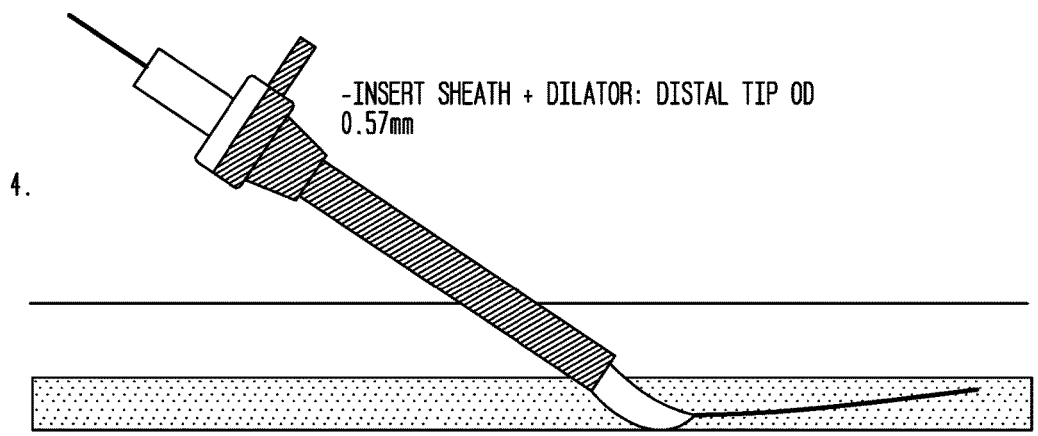
4.
- INSERT SHEATH + DILATOR: DISTAL TIP OD 0.57mm
*DISTAL TAPER PORTION MAY BE BENDABLE WITHIN BLOOD VESSEL BECAUSE OF VERY THIN (AND NO REINFORCING MEMBER)
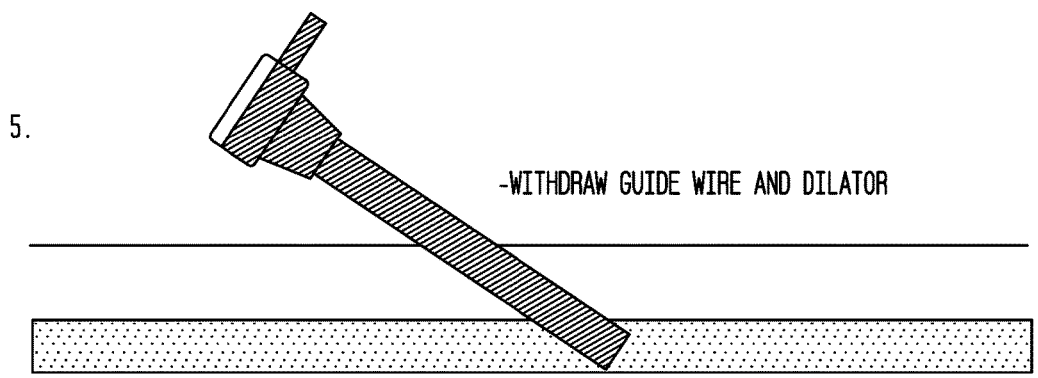
5.
- WITHDRAW GUIDE WIRE AND DILATOR

21G STEP NEEDLE

MICRO ACCESS KIT
TIF SHEATH
0.021" GUIDE WIRE
21G STEP NEEDLE
TIF DILATOR
(0.021" END HOLE)

MICROACCESS KIT COMPRISING A TAPERED NEEDLE

CROSS REFERENCE TO RELATED APPLICATIONS

This application is a continuation of U.S. application Ser. No. 13/421,404, filed Mar. 15, 2012, which claims benefit of U.S. Provisional Application No. 61/453,894 filed Mar. 17, 2011. The entire contents of each and every foregoing application are hereby incorporated herein by reference.

BACKGROUND OF THE TECHNOLOGY

The present technology is related to the field of interventional procedures and mechanisms, particularly to interventional guiding systems and particularly to assemblies of needles, guidewires, dilators and sheaths that are useful for guiding and maintaining the access into a patient's body for interventional procedures.

It is often desirable to access the interior of a patient's body, for example, the interior lumen of a blood vessel or the digestive tract, in connection with surgery or other interventional procedures. This is often done through multiple steps, including the use of micropuncture mechanisms and devices, followed by the use of devices that introduce mechanisms and devices into the interior of the patient's body, such as the interior of a blood vessel (for example, an artery or vein).

Current micropuncture needles in the art are designed with a "straight" shaft (also known as a pipe). Moreover, current micropuncture kits generally contain an access needle and several progressively larger dilators, which are inserted and removed in incremental steps. This design necessitates multiple steps between the initial accessing of the patient's interior, while progressively larger instruments are inserted into the puncture, to a final point where the final dilator can be comfortably inserted into the patient. However, this multistep process can take some time, and often involves the insertion and removal of several different objects into and out of the patient's body. Thus, great expertise and dexterity are required, and multiple steps with multiple devices can lead to a greater risk of error and injury.

Thus, a need exists for streamlined processes in connection with interventional procedures, as well as kits that comprise the various parts required, permitting ease of use, patient comfort and decreased patient recovery time.

SUMMARY OF THE TECHNOLOGY

In one embodiment according to the present technology, there is described a method for accessing an interior of a human, the method comprising the following steps:

(a) providing a guide wire comprising an elongated body and an outer diameter;

(b) providing a hollow needle comprising a distal portion having an outer diameter and an inner diameter and a proximal portion having an outer diameter and an inner diameter, the outer diameter of the proximal portion being greater than the outer diameter of the distal portion, the inner diameter of the distal portion and the inner diameter of the proximal portion being greater than the outer diameter of the guide wire;

(c) providing a introducer, the introducer comprising a sheath including a body, a distal portion, a distal tip and a lumen therethrough and a dilator including a body, a distal tapered portion, a distal tip and a lumen therethrough; the lumen of the dilator having an inner diameter greater than the outer diameter of the guide wire, the sheath being removably engaged to the dilator and the distal tapered portion of the dilator projecting from the distal tip of the sheath, the distal tip of the dilator having an outer diameter smaller than the outer diameter of the proximal portion of the hollow needle;

(d) inserting the hollow needle through a site on a skin so as to make a hole in the skin;

(e) placing the guide wire through the hollow needle and into an interior lumen;

(f) removing the hollow needle while leaving the guide wire in place;

(g) advancing the introducer over the guide wire through the lumen of the dilator and into the interior lumen so that the distal tapered portion of the dilator can easily insert and expand the hole made by the hollow needle; and, (h) removing the dilator and the guide wire, leaving the sheath inserted into the hole through its distal tip.

In another embodiment, the instant disclosure describes a kit for accessing the interior of a human, the kit comprising: a guide wire comprising an elongated body and an outer diameter; a hollow needle comprising a distal portion having an outer diameter and an inner diameter and a proximal portion having an outer diameter and an inner diameter, the outer diameter of the proximal portion is greater than the outer diameter of the distal portion, the inner diameter of the distal portion and the inner diameter of the proximal portion are greater than the outer diameter of the guide wire; and an introducer comprising a sheath including a body, a distal portion, a distal tip and a lumen therethrough and a dilator including a body, a distal tapered portion, a distal tip and a lumen therethrough, the lumen of the dilator having an inner diameter greater than the outer diameter of the guide wire, the sheath removably engaged the dilator and projected the distal tapered portion of the dilator from the distal tip of the sheath, the distal tip of the dilator having an outer diameter smaller than the outer diameter of the proximal portion of the hollow needle.

In another embodiment, the instant disclosure also describes a hollow needle for accessing the interior of a human, the hollow needle comprising: a distal tip for penetrating a skin, a distal portion having an outer diameter and an outer surface and a proximal portion having an outer diameter and an outer surface, the outer diameter of the distal portion is smaller than the outer diameter of the proximal portion, a tapered portion smoothly varying an outer diameter from the outer diameter of the proximal portion to the outer diameter of the distal portion, the outer diameter of the proximal portion being greater than the outer diameter of the distal portion.

Further aspects, features and advantages of the present technology will be better appreciated upon a reading of the detailed description of the technology.

BRIEF DESCRIPTION OF THE FIGURES

FIGS. 1-4 illustrate a conventional multi-step procedure for introducing an interventional guiding system;

FIGS. 5-6 illustrate the steps of the new procedure/method in accordance with the instant technology;

DETAILED DESCRIPTION OF THE TECHNOLOGY

Current known needles used for micropuncture are designed with a "straight" shaft (pipe). That is, the needle is of uniform diameter from its proximal end (which is attached to the syringe portion that is held by the user) to its distal end (which is inserted into the patient). This generally leads to a procedure in which the user first punctures the patient's skin with a small needle, then inserts a dilator of a small diameter, and subsequently inserts one or more dilators with progressively larger diameters, as a way of easing the patient's puncture from a smaller opening to a larger opening, and enabling the insertion of a larger diameter dilator as part of the interventional procedure.

As currently used in the art, the current process of introducing a dilator or sheath or other component of any interventional guiding system requires multiple steps. First, a needle is inserted into the patient's skin into the lumen of the patient's interior. Then a guide wire is inserted through the needle and into the patient's interior lumen. The needle is withdrawn, leaving the opening and the guide wire. A dilator (which comprises an inner dilator and an outer dilator) is then threaded on the needle and inserted into the patient's interior. The inner dilator and guidewire are withdrawn, leaving the outer dilator in place to hold the puncture area open. A second guidewire is inserted, the second guidewire and outer dilator are withdrawn, and ultimately a sheath and second dilator are inserted, and the second guidewire and second dilator are withdrawn, leaving the sheath. This multistep procedure illustrated in FIG. 1 through FIG. 4 is necessary in order to minimize injury to the patient.

In contrast, it has been discovered herein that this multi-step procedure can be avoided by using a unique needle or kit as described herein in accordance with the present technology. In certain embodiments, such needle has a smoothly tapered transition between a smaller diameter tip and a larger diameter shaft along the length of the cannula. As used herein, the terms "cannula" and "needle" are used interchangeably, and refer to the same thing.

Figure 1:
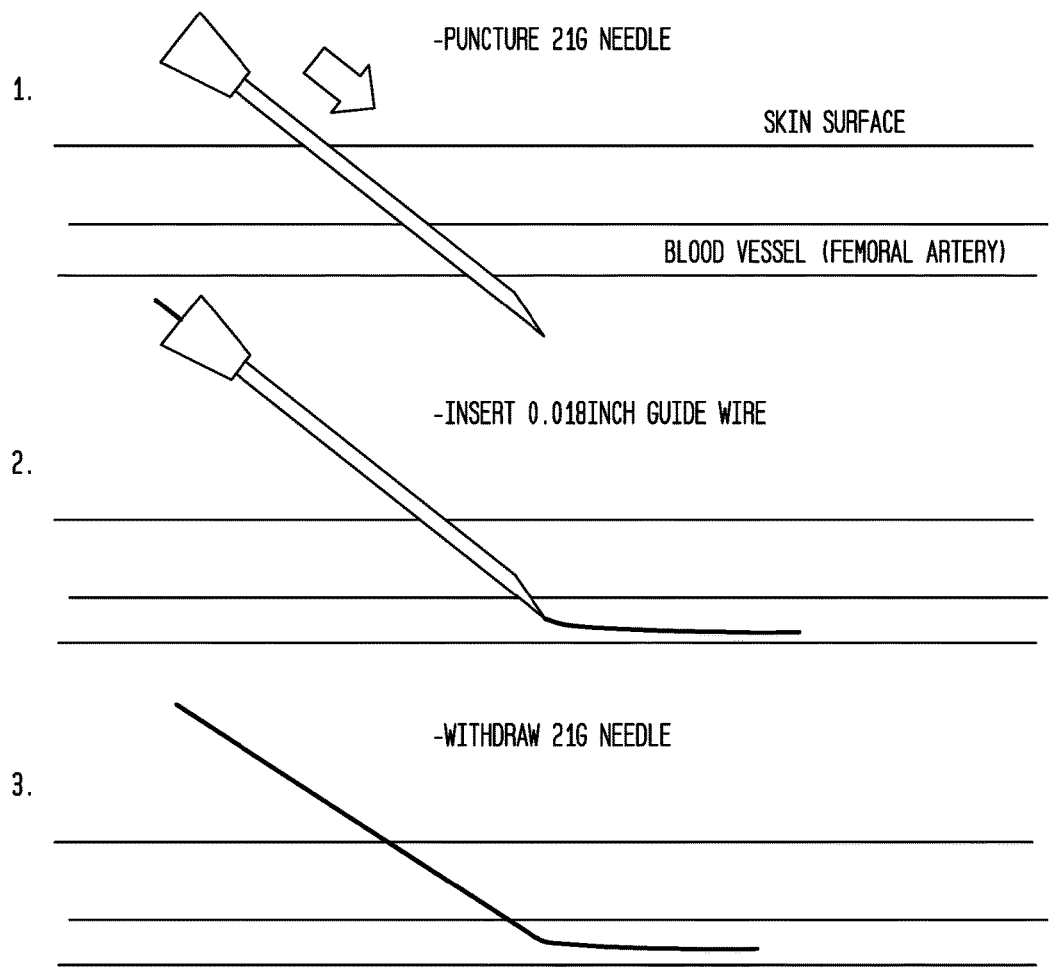
Figure 2:
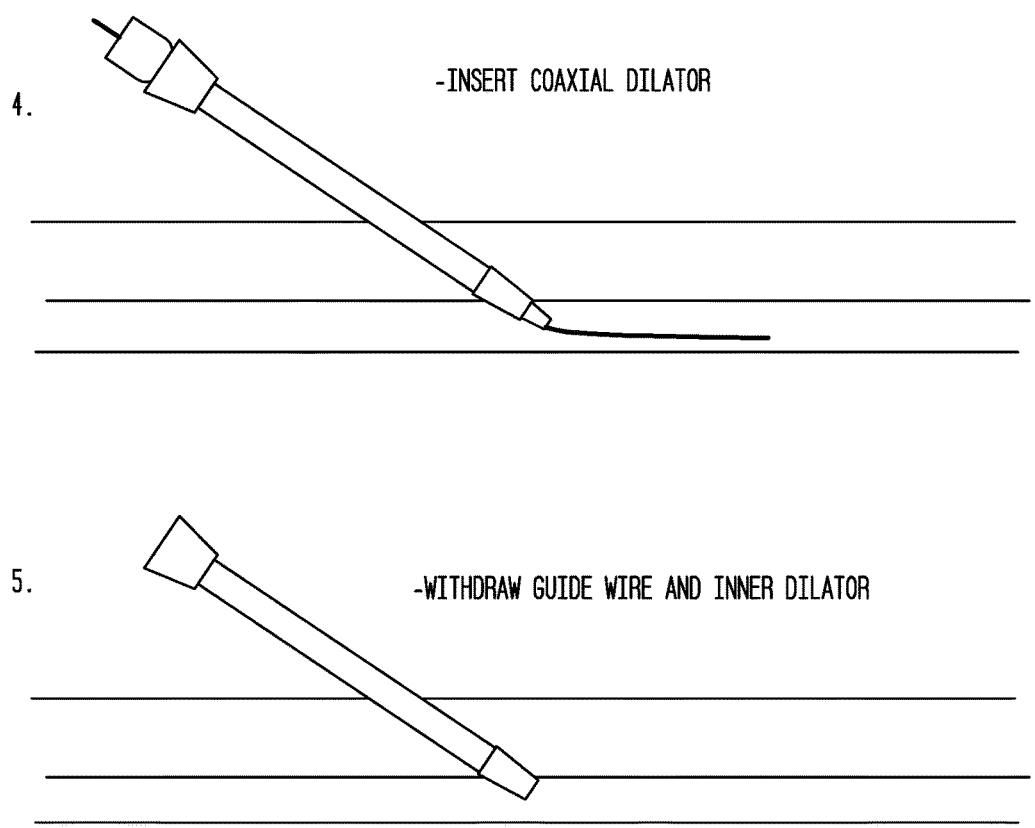
Figure 3:
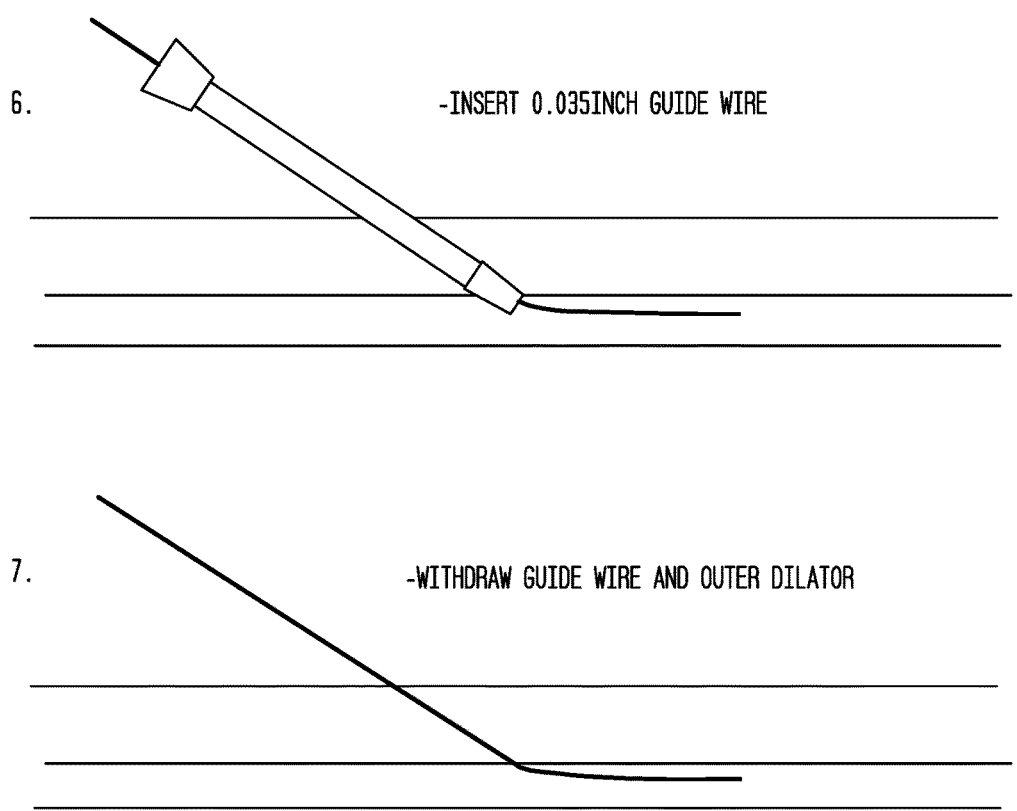
Figure 5:
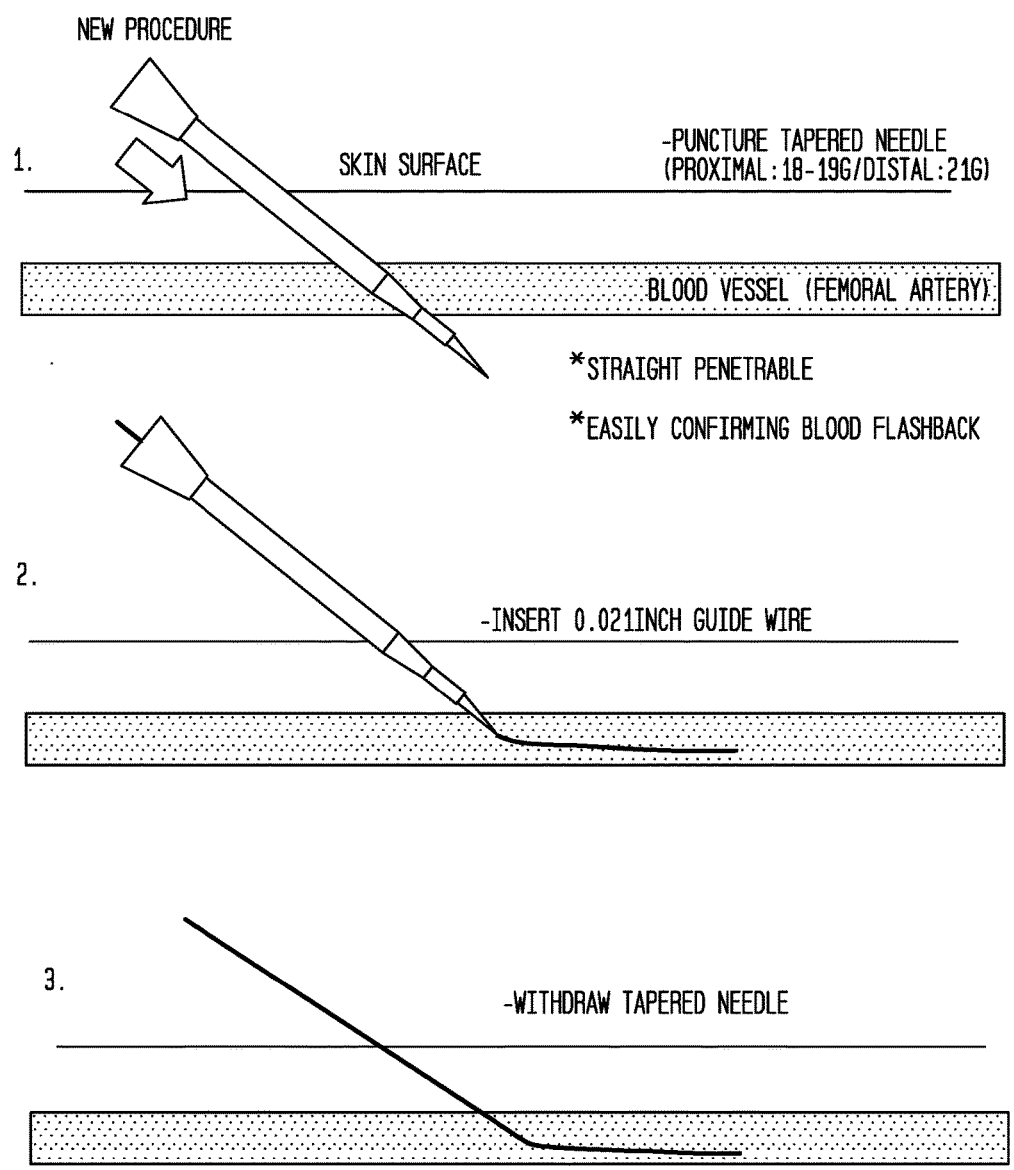

In accordance with the embodiments described herein, the innovative method of the instant technology is illustrated in FIGS. 5-6, such that a guide wire is provided comprising an elongated body and an outer diameter.

A hollow needle is also provided comprising a distal portion having an outer diameter and an inner diameter and a proximal portion having an outer diameter and an inner diameter, the outer diameter of the proximal portion being greater than the outer diameter of the distal portion, the inner diameter of the distal portion and the inner diameter of the proximal portion being greater than the outer diameter of the guide wire.

An introducer is also provided and which comprises a sheath including a body, a distal portion, a distal tip and a lumen therethrough and a dilator including a body, a distal tapered portion, a distal tip and a lumen therethrough; the lumen of the dilator having an inner diameter greater than the outer diameter of the guide wire, the sheath being removably engaged to the dilator and the distal tapered portion of the dilator projecting from the distal tip of the sheath, the distal tip of the dilator having an outer diameter smaller than the outer diameter of the proximal portion of the hollow needle.

The hollow needle is inserted through a site on a skin so as to make a hole in the skin. The guide wire is then placed through the hollow needle and into an interior lumen, followed by the removal of the hollow needle while leaving the guide wire in place.

The introducer is then advanced over the guide wire through the lumen of the dilator and into the interior lumen so that the distal tapered portion of the dilator can easily insert and expand the hole made by the hollow needle.

The dilator and guide wire are then removed leaving the sheath inserted into the hole through its distal tip.

In other embodiments, the present technology contemplates kits comprising such needles and methods of accessing the interior of a patient's body comprising the mechanisms and kits of the present technology.

Tapered Needle

Figure 7:
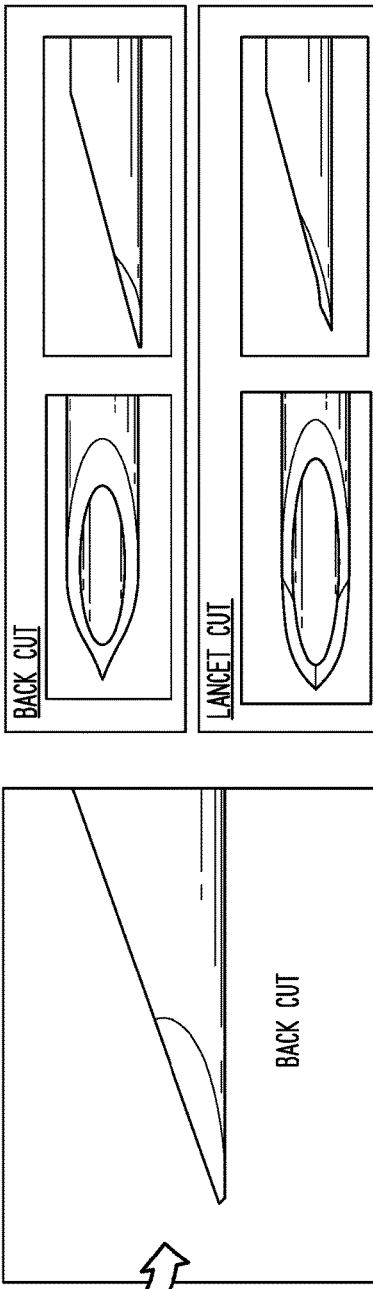
FIG. 7 illustrates different views of a 21G step needle in accordance with the instant technology.

In certain embodiments of the present technology, a needle is used that is tapered. As used throughout the present disclosure, "tapered" means that the proximal end of the needle and the distal end of the needle do not have the same diameter. For example, a tapered needle in accordance with the present technology may have a proximal end (closer to the plunger) equivalent to a 18 gauge to 21 gauge needle, or 18 gauge, 19 gauge, 20 gauge or 21 gauge; that then tapers to a distal end equivalent to 21 gauge, or 20 gauge to 25 gauge, or 20 gauge, 21 gauge, 22 gauge, 23 gauge, 24 gauge or 25 gauge. In certain embodiments, the needle tapers from an 18 gauge or 19 gauge distal end to a 21 gauge proximal end. In other embodiments, the needle may taper over a larger or smaller diameter difference (for example, 18 gauge to 22, 23, 24 or 25 gauge, or 21 gauge to 24 gauge), depending on the needs of the patient and the interventional procedure. FIG. 7 illustrates an exemplary 21 G step needle.

Figure 8:
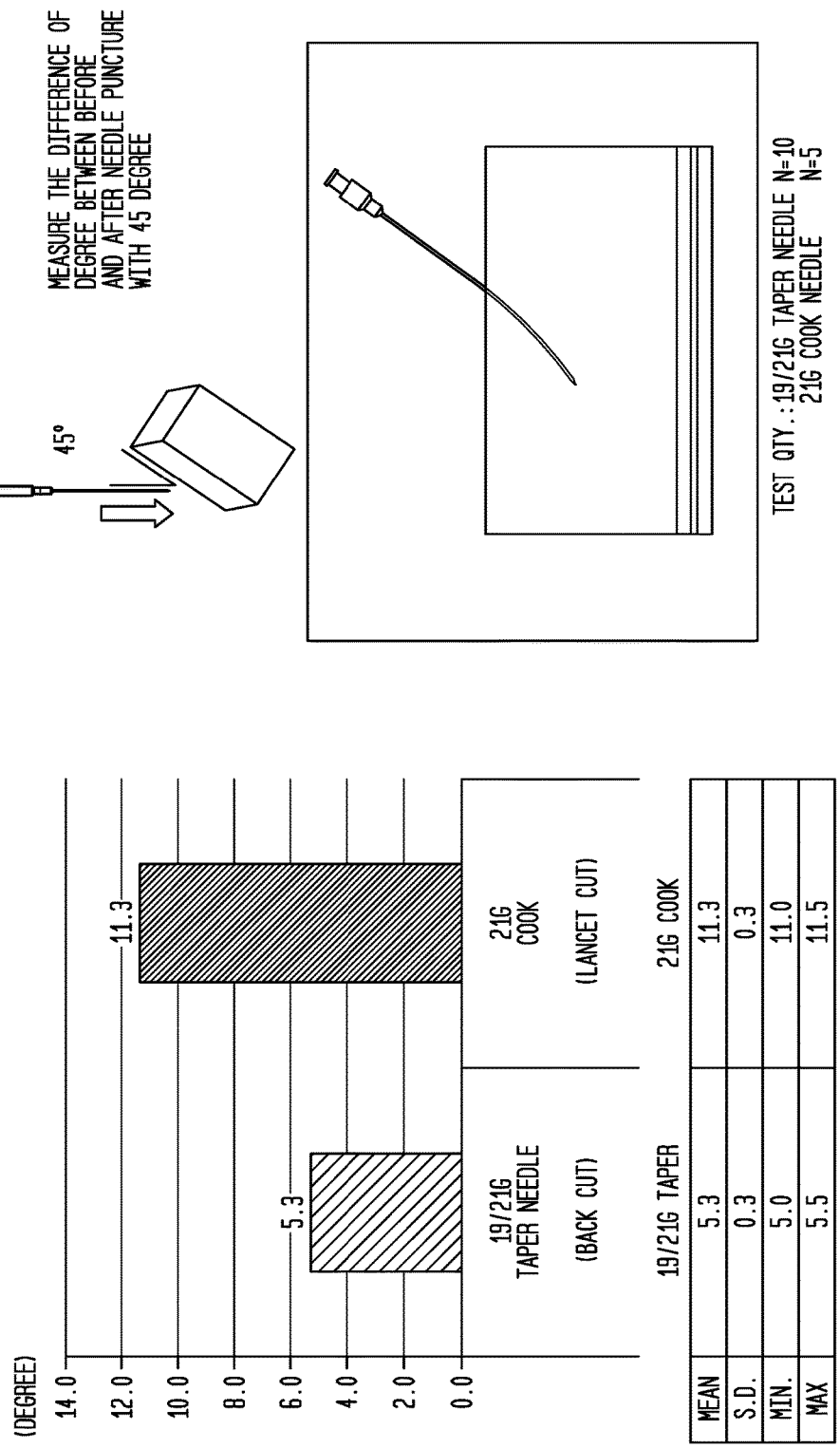
FIGS. 8-9 illustrate a comparison between a tapered needle and a conventional Cook needle.
Figure 9:
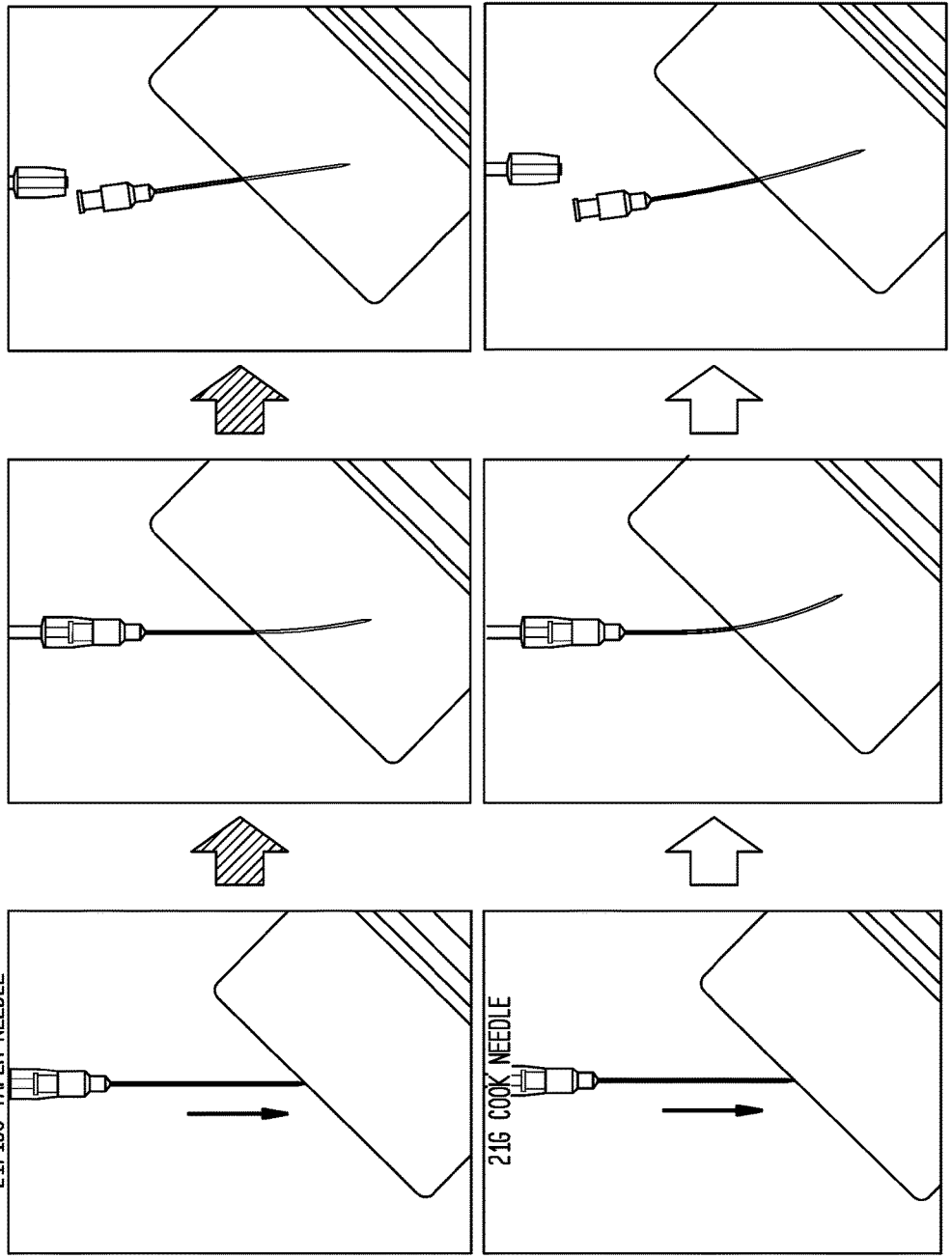

Any degree of taper that is useful and desired is contemplated within the scope of the technology. For example, the tapered portion of the needle may, in certain embodiments, comprise consecutive tapered portions with different angles. In one exemplary embodiment, the needle may be divided into multiple regions In certain embodiments, the needles of the present technology may be useful for femoral access. The advantage is that the distance from the surface of the patient's body to the femoral artery is relatively long (in certain embodiments, about 60 mm (2.36 inches)). In certain embodiments of the present technology, the tapered needle is stiffer than known needles used in the art, and therefore is less likely to bend after insertion and during its journey to the targeted area; additionally, the stiffer shaft helps to achieve penetration of hard tissue within the leg, such as any scar tissue or calcification that may be present, with minimal discomfort to the patient and maximum ease to the surgeon, nurse or other medical personnel. Another advantage is that a smaller puncture hole on the patient's skin is required, thus minimizing bleeding and the likelihood of complications. Thus, the user can enjoy the benefit of a smaller puncture hole initially, but also a larger point of entry eventually, which then eliminates the need for successively larger dilators to be inserted. The advantages of the needles of the present technology are illustrated further in the present disclosure, describing the comparison between a tapered needle and a known Cook needle, as seen in FIG. 8-9. In FIGS. 8 and 9, a tapered needle in accordance with the present technology was tested in comparison to a known Cook needle.

The proximal portion of the tapered needle is thicker and stiffer than the Cook needle shaft and the distal portion is stiffer than a comparable sized Cook needle. Accordingly the tapered needle penetrates straighter than the Cook needle.

The results of testing tapered needle and the Cook needle showed that the tapered needle could easily catch the patient's blood vessel since it could penetrate relatively straight while the Cook needle required several penetrations due to non-straight penetration. This is The taper may be such that, for example, a spot on the proximal portion of the needle has a diameter of about 40 to about 70% (21G/18G), and about 10 to about 50% (21G/19G), greater than a spot on the distal portion of the needle.

Figure 10:
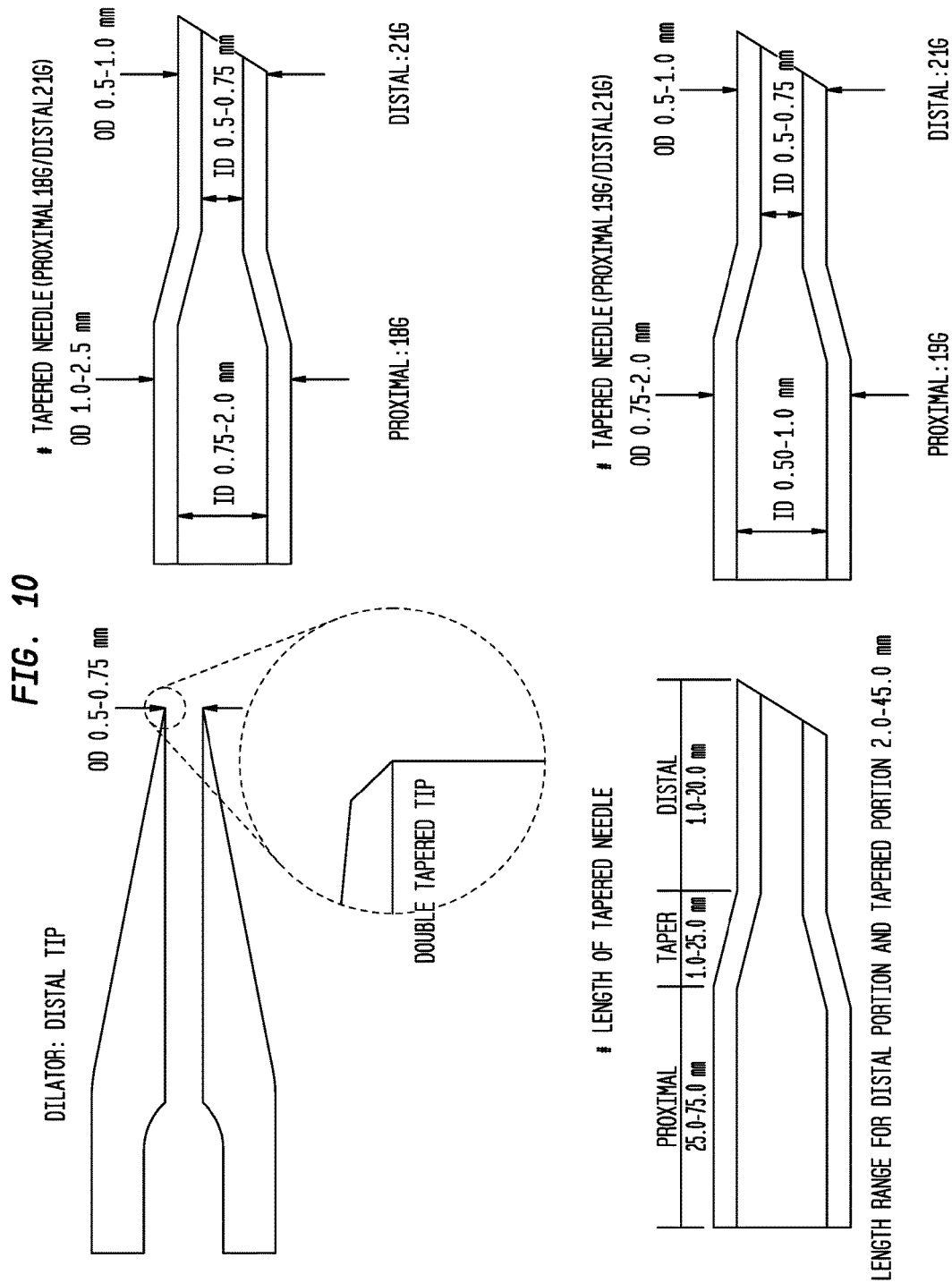
FIG. 10-11 illustrated tapered needles and degrees of tapering.
Figure 11:
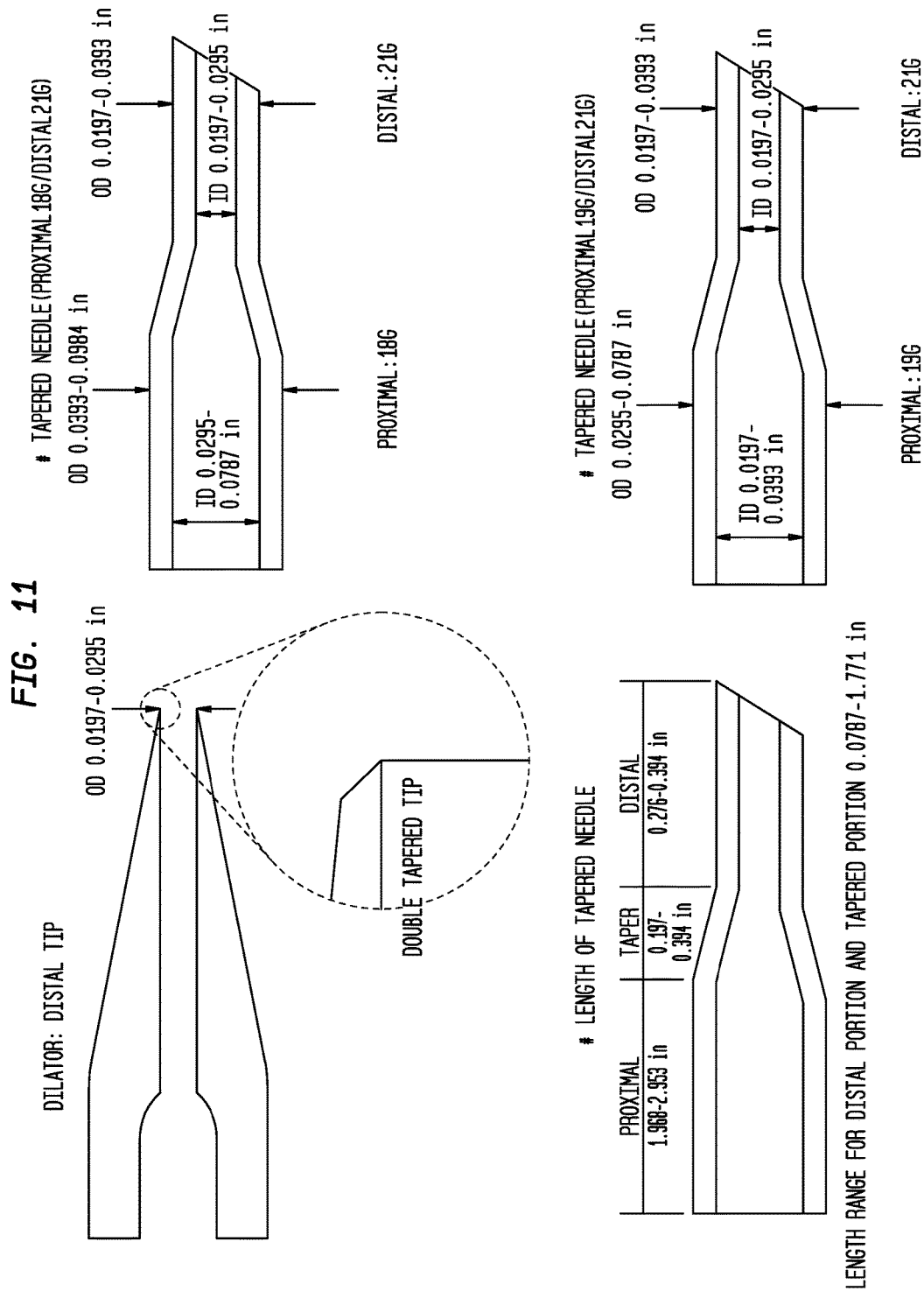

Examples of tapered needles and degree of tapering can be seen in FIG. 10 and FIG. 11. Numbers presented in those Figures are in metric (mm) in FIG. 10 and English (inches) in FIG. 11. All numbers are estimates—that is, viewing each of FIG. 10 and FIG. 11 from the top left to the bottom right:

The outer diameter (OD) of the dilator in the embodiment pictured therein is about 0.5 to about 0.75 mm (about 0.0197 to about 0.0295 inches);

For the tapered needle (proximal 18G/distal 21G), the OD on the larger (proximal) side of the taper is about 1.0 to about 2.5 mm (about 0.0393 to about 0.0984 inches); the OD on the smaller (distal) side of the taper is about 0.5 to about 1.0 mm (about 0.0197 to about 0.0393 inches); the inner diameter (ID) on the larger (proximal) side of the taper is about 0.75 to about 2.0 mm (about 0.0295 to about 0.0787 inches); and the ID on the smaller (distal) side of the taper is about 0.5 to about 0.75 m (about 0.0197 to about 0.0295 inches);

For the length of tapered needle, the proximal portion is about 25.0 to about 75.0 mm (about 0.984 to about 2.953 inches); the tapered portion is about 1.0 to about 25.0 mm (about 0.0393 to about 0.984 inches); the distal portion is about 1.0 to about 20.0 mm (about 0.0393 to about 0.787 inches);

The length range for distal portion+tapered portion is about 2.0 to about 45.0 mm (about 0.0787 to about 1.771 inches); and For the tapered needle (proximal 19 G/distal 21G), the OD on the larger (proximal) side of the taper is about 0.75 to about 1.0 mm (about 0.0197 to about 0.0393 inches); the OD on the smaller (distal) side of the taper is about 0.5 to about 1.0 mm (about 0.0197 to about 0.02393 inches); the ID on the larger (proximal) side of the taper is about 0.50 to about 1.0 mm (about 0.0197 to about 0.0393 inches); and the ID on the smaller (distal) side of the taper is about 0.5 to about 0.75 m (about 0.0197 to about 0.0295 inches).

In certain embodiments, not only the needle but also the dilator may comprise a tapered portion. In other embodiments, any of the needle or dilator may be doubly tapered or even tapered in more than two different sections—that is, comprising, for example, a first portion having a first diameter, a second portion having a second diameter and a third portion having a third diameter, and so on. In certain embodiments, a greater number of tapered sections may provide for a smoother taper and therefore, greater comfort for the patient and ease of use for the medical personnel.

In certain embodiments, any portion of the tapered needle of the technology may comprise etching on its surface, in such a manner that it will enhance visibility by the user (for example, radiopaque visibility). For example, the etching may be in the form of a helical or spiral pattern formed by grooves etched around the surface of the needle, or a pattern of spots etched on the surface of the needle in a manner that the user can refer to the areas of different surface roughness to discern the angle or orientation of the needle.

Guidewire

In the current art, the first guidewire is generally one of 0.035 or 0.038 inches diameter (0.889 inches or 0.965 inches or 4-5 French), to ease the transition of the opening and prevent injury to the patient. Thereafter, a dilator is used as part of an introducer kit; the dilator generally has a 4-9 French diameter (or ⅛ inch). These steps are followed by steps of inserted a larger second guidewire and a larger second dilator. However, in certain embodiments, the present technology provides the tapered needle (for example, a 19 gauge or 21 gauge needle), which when inserted into the patient's skin, creates a larger opening. As a result, a larger diameter and stiffer guidewire can immediately be inserted, obviating the need for multiple dilators. In other words, the medical personnel can go directly from the microaccess step to the introducer step.

The guidewire at any stage of the methods of the present technology may have a diameter of about 0.015 to about 0.018 inches (these are particularly useful with a 21 gauge needle) or about 0.015 to about 0.021 inches, or about 0.035 or about 0.038 inches.

Introducer

In certain embodiments, the microaccess kits and mechanisms of the present technology may include an introducer. The introducer may comprise a dilator and a sheath that are removably engaged to each other. The dilator may comprise a body, a distal tapered portion (also referred to herein as the "dilator tip" or the "distal tip") and a lumen therethrough. The sheath may comprise a body, a distal portion, a distal tip (which may or may not be tapered, in the case of the sheath), and a lumen therethrough. The sheath may be removably engaged to the dilator and the distal portion of the dilator may have an outer diameter smaller than the outer diameter of the proximal portion of the hollow needle. This is because it adds to patient comfort when the medical personnel do not have to force a larger tube into the small hole that is created by the needle puncture. In certain embodiments, the lumen of the dilator has an inner diameter greater than the outer diameter of the guide wire. This facilitates smooth entry and movement of the guide wire within the lumen of the dilator.

In certain embodiments, the dilator tip and/or the sheath distal tip may comprise a tapered portion. In other embodiments, any of the dilator or sheath may be doubly tapered or even tapered in more than two different sections—that is, comprising, for example, a first portion having a first diameter, a second portion having a second diameter and a third portion having a third diameter, and so on. In certain embodiments, a greater number of tapered sections may provide for a smoother taper and therefore, greater comfort for the patient and ease of use for the medical personnel.

An advantage of the present technology is that the introducer may be used as an integral part of the microaccess kit—unlike the kits known in the art, multiple introducers are not required; nor are multiple steps required before insertion of the introducer into the patient's body.

Kits and Methods

Figure 12:
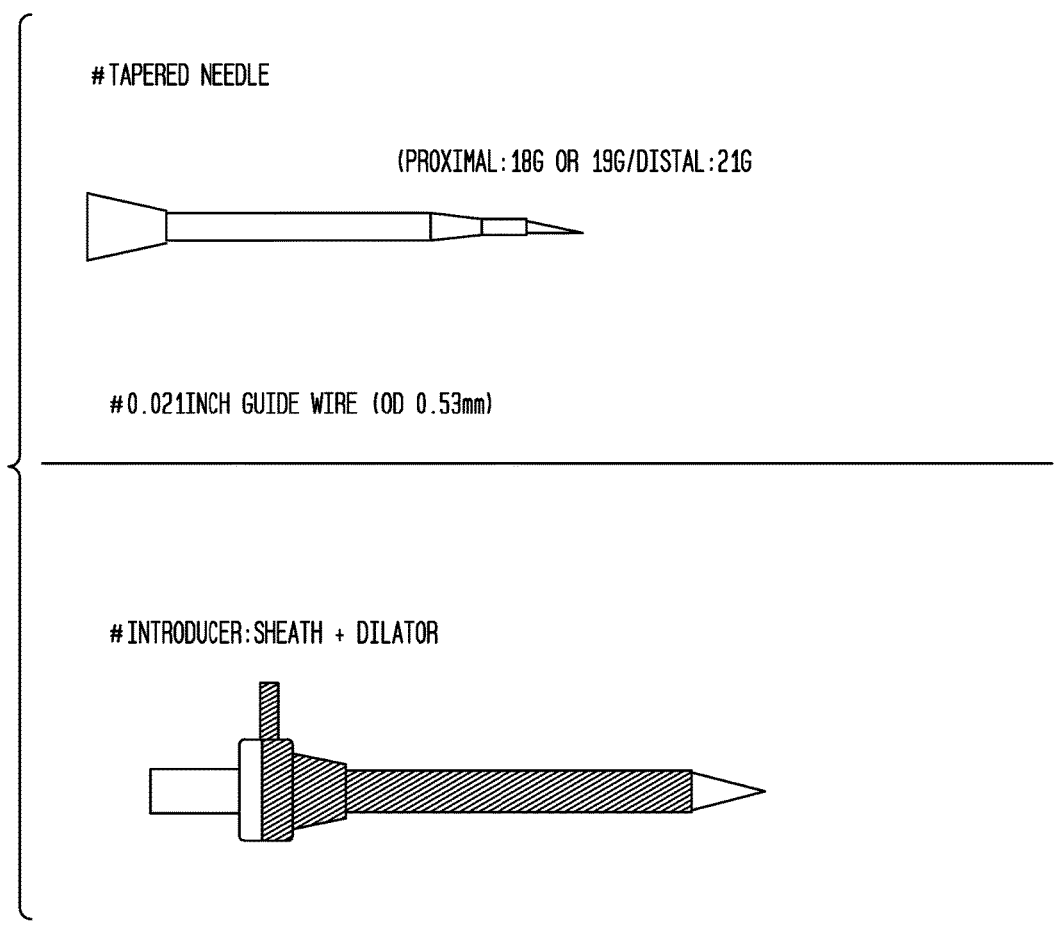
FIGS. 12-13 illustrate micro access kits for use in accordance with the present technology.
Figure 13:
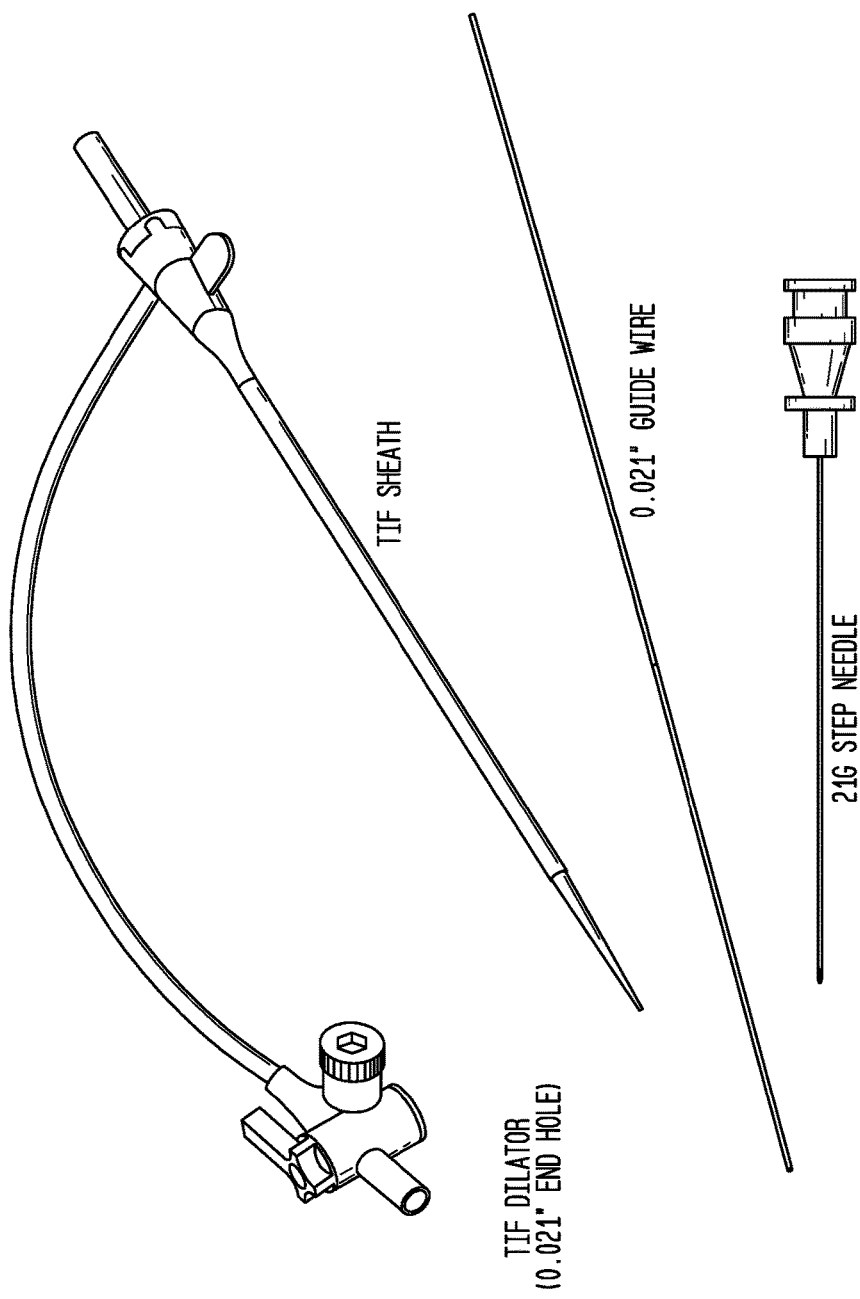

In certain embodiments, kits of the present technology comprise any of the following: a tapered needle; a dilator and a sheath; and a guide wire. One advantage is that a kit of the present technology can replace separate microaccess and introducer kits that are currently used in the art, by combining them into a single kit comprising a needle, a dilator and sheath and a guide wire. Because the needle is tapered, it is easily inserted into the patient's skin and then upon further insertion, "stretches" out the puncture in a smooth way that facilitates relatively painless insertion of the dilator and subsequent objects that may be inserted therein. An exemplary kit including a tapered needle and an introducer (sheath and dilator) is illustrated in FIG. 12 and FIG. 13.

In other embodiments, the kit comprises a tapered needle; and a sheath/dilator (either separately provided for combination together, or already combined together) that has an interior lumen communicating with a dilator tip, any portion of the dilator tip having a diameter that is smaller than the shaft diameter of the needle. It has been found that this may improve the smooth entrance of the dilator. For example, the tapered needle may have an inner diameter near its tip of about 0.58 mm, but the outer diameter of the dilator tip may be about 0.57 mm. In certain embodiments, these diameters may differ from each other by about 2% to about 15%, about 5% to about 10% or about 5% or about 10%.

In still other embodiments, the dilator further comprises a hollow reinforcing member, for example, a tube, which can be made from plastic or any polymeric material (for example, ETFE) or of metal. The tube may serve the purpose of providing further reinforcement of the stiffness of the dilator as well as stability, preserving the integrity of the dilator. The tube may be disposed at any point along the interior of the dilator, or even on the exterior of the dilator. In certain embodiments, the length of the tube may end before the distal portion of the dilator, or at the dilator tip, thus preserving flexibility on the area of the dilator immediately adjacent and in contact with the area of the dilator that touches the body All embodiments described herein are illustrative and in no way limit the scope of the technology, and the technology may be embodied in other forms not explicitly described here, without departing from the spirit thereof It should thus be understood that the foregoing description is only illustrative of the present technology. Various alternatives and modifications can be devised by those skilled in the art without departing from the technology. Accordingly, the present technology is intended to embrace all such alternatives, modifications and variations that fall within the scope of the appended claims.

What is claimed is:

1. An introducer needle assembly comprising a needle with a single hollow lumen therethrough, the needle comprising a proximal portion having a proximal outer diameter and proximal inner diameter, and a distal portion having a distal outer diameter and a distal inner diameter, the needle being tapered between the proximal portion and the distal portion such that the proximal outer diameter is greater than the distal outer diameter and an inner diameter of the distal portion is smaller than an inner diameter of the proximal portion, wherein the needle tapers from a diameter of a 19 gauge needle at its proximal portion to a diameter of a 21 gauge needle at its distal-most tip, the needle having a stiffness that provides less than 6 degrees of bend when at least half of the needle is inserted at a 45 degree angle into a test fixture representative of a human body.

2. The introducer needle assembly of claim 1, wherein the tapering between the proximal portion and the distal portion comprises at least two tapered portions.

3. The introducer needle assembly of claim 2, wherein at least two of the tapered portions have different angles.

4. The introducer needle assembly of claim 1, wherein at least a portion of the needle is echogenic.

5. An introducer needle assembly comprising a needle with a single hollow lumen therethrough, the needle comprising a proximal portion having a proximal outer diameter and proximal inner diameter, and a distal portion having a distal outer diameter and a distal inner diameter, the needle being tapered between the proximal portion and the distal portion such that the proximal outer diameter is greater than the distal outer diameter and an inner diameter of the distal portion is smaller than an inner diameter of the proximal portion, wherein the needle tapers from a diameter of an 18 gauge needle at its proximal portion to a diameter of a 21 gauge needle at its distal-most tip, the needle having a stiffness that provides less than 6 degrees of bend when at least half of the needle is inserted at a 45 degree angle into a test fixture representative of a human body.

6. The introducer needle assembly of claim 5, wherein the tapering between the proximal portion and the distal portion comprises at least two tapered portions.

7. The introducer needle assembly of claim 6, wherein at least two of the tapered portions have different angles.

8. The introducer needle assembly of claim 5, wherein at least a portion of the needle is echogenic.

9. A hollow needle for accessing the interior of a human, the hollow needle comprising:
   a distal tip for penetrating a site on skin of said human,
   a distal portion having an outer diameter and an outer surface and a proximal portion having an outer diameter and an outer surface, the outer diameter of the distal portion is smaller than the outer diameter of the proximal portion,
   a tapered portion smoothly varying an outer diameter from the outer diameter of the proximal portion to the outer diameter of the distal portion, the outer diameter of the proximal portion being greater than the outer diameter of the distal portion, at least a portion of the tapered portion being configured to penetrate the site on the skin of said human, wherein the proximal portion has a size of a 18 gauge or 19 gauge needle and a distal-most tip has a size of a 21 gauge needle, the needle having a stiffness that provides less than 6 degrees of bend when at least half of the needle is inserted at a 45 degree angle into a test fixture representative of a human body.

10. The hollow needle of claim 9, wherein an inner diameter of the distal portion is smaller than an inner diameter of the proximal portion.

11. The hollow needle of claim 9, wherein the distal tip comprising a lancet cut or a backcut.

12. The hollow needle of claim 9, wherein the tapered portion comprises at least two consecutive tapered sections with different angles.

13. The hollow needle assembly of claim 9, wherein at least a portion of the needle is echogenic.

* * * * *